United States Patent

Stache et al.

Patent Number: 5,362,721
Date of Patent: Nov. 8, 1994

[54] CORTICOID-17-ALKYL-CARBONATES SUBSTITUTED IN THE 17-POSITION, PROCESS FOR THEIR PREPARATION AND PHARMACEUTICALS CONTAINING THEM

[75] Inventors: Ulrich Stache, Hofheim am Taunus; Walter Dürckheimer, Hattersheim am Main; Hans G. Alpermann, Königstein/Taunus; Walter Petri, Wiesbaden, all of Germany

[73] Assignee: Hoechst Aktiengesellschaft, Frankfurt am Main, Germany

[21] Appl. No.: 15,041

[22] Filed: Feb. 8, 1993

Related U.S. Application Data

[63] Continuation of Ser. No. 742,334, Aug. 8, 1991, abandoned.

[30] Foreign Application Priority Data

Aug. 10, 1990 [DE] Germany .............. 4025342

[51] Int. Cl.$^5$ .................................. C07J 9/00
[52] U.S. Cl. .......................... 514/179; 514/180; 514/181; 552/572; 552/573; 552/574; 552/576; 552/577; 552/597
[58] Field of Search ............ 514/179, 180, 181; 552/572, 576, 597, 573, 574, 577

[56] References Cited

U.S. PATENT DOCUMENTS

| | | | |
|---|---|---|---|
| 3,621,014 | 11/1971 | Stache et al. | 260/239.55 |
| 4,242,334 | 12/1980 | Stache et al. | 424/243 |
| 4,377,575 | 3/1983 | Stache et al. | 552/597 |

FOREIGN PATENT DOCUMENTS

| | | |
|---|---|---|
| 4975 | 10/1979 | European Pat. Off. . |
| 0136586A3 | 4/1985 | Germany . |
| 2079755A | 1/1982 | United Kingdom . |

OTHER PUBLICATIONS

Arzneim.-Forsch./Drug Res. 35 (I), No. 6 (1985) pp. 939-946, Vogel et al.—Prednicarbate.

*Primary Examiner*—Johann Richter
*Assistant Examiner*—Kimberly J. Kestler
*Attorney, Agent, or Firm*—Finnegan, Henderson, Farabow, Garrett & Dunner

[57] ABSTRACT

The disclosed invention includes corticoid-17-alkylcarbonates substituted in the 17-position, a process for their preparation and pharmaceuticals containing them. These corticoid-17-alkylcarbonates have the following formula I

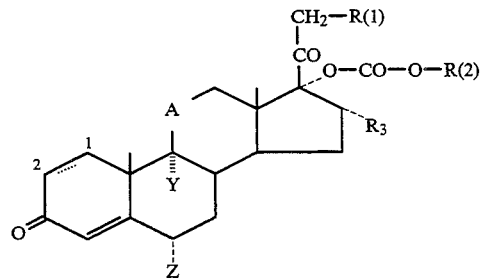

where A is CHOH in any desired steric arrangement, C=O or $CH_2$;

Y is H, F, or Cl; Z is H, F or $CH_3$; R(1) is O-acyl, carbonylalkyl, alkylsulfonate or arylsulfonate;
R(2) is branched alkyl or $(CH_2)_{2-4}$—$OCH_3$ and
R(3) is H or methyl. They have excellent local and topical antiinflammatory action. They are distinguished by a particularly good ratio of local to systemic antiinflammatory activity and in some cases also show stronger local antiinflammatory activities than their isomeric corticoid-17-alkylcarbonates having a linear alkyl group in the 17-alkylcarbonate moiety.

4 Claims, No Drawings

CORTICOID-17-ALKYL-CARBONATES SUBSTITUTED IN THE 17-POSITION, PROCESS FOR THEIR PREPARATION AND PHARMACEUTICALS CONTAINING THEM

This application is a continuation, of application Ser. No. 07/742,334, filed Aug. 8, 1991, now abandoned.

DESCRIPTION

The invention relates to corticoid-17-alkylcarbonates of the formula I

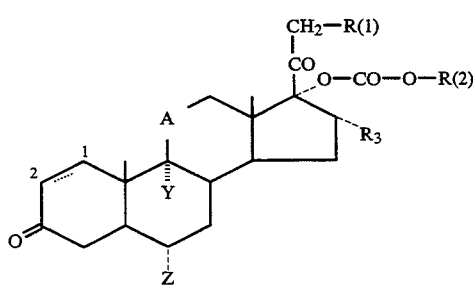

in which:

A is CHOH in any desired steric arrangement, $CH_2$ or $C=O$,

Y is hydrogen, fluorine or chlorine,

Z is hydrogen, fluorine or methyl,

R(1) is F, Cl, Br, I, O-acyl of the formula II: —O—CO—$(CH_2)_n$—R(4), oxycarbonyloxyalkyl of the formula III: —O—CO—O—$(CH_2)_n$-R(4) or alkylsulfonate or arylsulfonate of the formula IV: —O—$SO_2$—R(5) where R(4) is equal to hydrogen, $(C_1-C_{10})$-alkyl, $(C_3-C_6)$-cycloalkyl or, if n=1, is fluorine, chlorine or bromine, R(5) is equal to $(C_1-C_4)$-alkyl, phenyl, chlorophenyl or methylphenyl, n is an integer from 0 to 4, R(2) is branched $(C_3-C_8)$-alkyl or—$(CH_2)_{2-4}$—$OCH_3$ and R(3) is hydrogen or α-methyl.

Compounds of the formula I are preferred where R(1), A, Y, Z and R(3) are as indicated and R(2) is equal to branched $(C_3+C_5)$-alkyl and —$(CH_2)_2$—$OCH_3$, R(5) is equal to methyl, ethyl, propyl or phenyl which is unsubstituted or substituted in the p-position by chlorine or methyl.

Compounds I are very particularly preferred where Y is equal to hydrogen and

Z is equal to hydrogen or methyl, and

R(2) is equal to —$CH(CH_3)_2$, —$CH_2$—$CH(CH_3)_2$, —$CH_2C(CH_3)_3$ or —$(CH_2)_2$—O—$CH_3$; and the bond between $C_1$ and $C_2$ is a single bond or a double bond, such as indicated by the dotted line in formula I.

The invention additionally also relates to a process for the preparation of compounds I, which comprises hydrolyzing compounds of the formula V

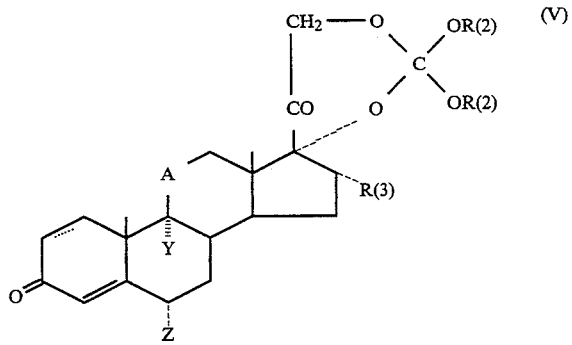

using a weak acid and esterifying the resulting 21-hydroxy compound with a halide or an anhydride of a carboxylic acid of the formula VI R(4)—$(CH_2)_n$—COOH      VI or a haloformate of the formula VII R(4)—$(CH_2)_n$—OCO—halogen or a sulfonyl halide of the formula VIII R(5)—$SO_2$—halogen      VIII and, if desired, reacting the resulting 21-sulfonic acid esters with halide salts to give 21-halides of the formula I where R(1) is equal to chlorine, bromine, iodine or fluorine. The invention furthermore relates to a process for the preparation of the compounds of the formula V, in which the basic corticosteroids of the formula VI

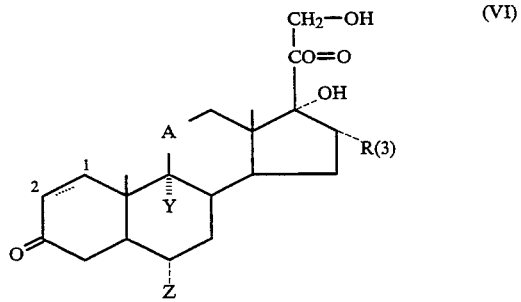

are reacted with tetraalkyl orthocarbonates, which are branched or substituted in the alkyl moiety, of the formula VII

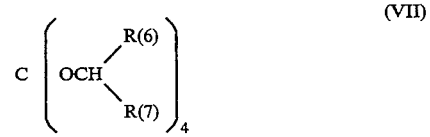

in inert solvents at temperatures of greater than 20° to 120° C., preferably up to the boiling point of the reaction mixtures, in particular at about 50° to 60° C.

In the formula VI, A, Y, Z and R(3) have the above-mentioned meanings,

R(6) is H or $CH_3$ and

R(7) is $CH_3$, $CH(CH_3)_2$, $C(CH_3)_3$ or $CH_2OCH_3$.

The preparation of compounds in which, at the same time, R(6) is H and R(7) does not contain a branched carbon chain is excluded.

The steroid-17,21-dialkylorthocarbonates of the formula V required as starting substances are prepared by the process according to German Patent No. 1,668,079. However, for the preparation of the 17,21-dialkylorthocarbonates of the formula V which are branched in the alkyl moiety and substituted by alkoxy groups, as a rule substantially higher reaction temperatures, usually greater than 50° C., and longer reaction times (twice to four times the reaction times) are necessary than is the case with the linear analogs according to German Patent No. 1,668,079 (HOE 68/ F 012).

The 21-hydroxy group, depending on whether it is intended to prepare a 21-alkylcarbonate, a 21-carboxylic acid derivative or a 21-alkyl- or -arylsulfonic acid ester of the underlying corticoid-17-alkylcarbonates, can be reacted with the acylating agents customary for this purpose:

a) For the preparation of 21-alkylcarbonates, alkyl chloroformates of the formula

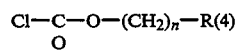

are preferably used in which R(4) has the meaning indicated for formula I. Methyl, ethyl, propyl or butyl chloroformate is preferably used.

b) For the preparation of 21-carboxylic acid esters, either carbonyl halides of the formula

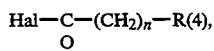

in which Hal is Cl, Br or I and R(4) has the meaning indicated for formula I, or carboxylic anhydrides of the formula $[OC-(CH_2)_n-R(4)]_2O$, in which R(4) has the meaning indicated for formula I, are used. For example, the following can be used: acetyl, propionyl, butyryl or valeryl chloride or anhydride, cyclopropanecarbonyl, cyclopentylpropionyl or enanthyl chloride.

c) For the preparation of 21-sulfonic acid esters, suitable sulfonyl halides are those of the formula $Cl-SO_2-R(5)$ in which R(5) has the meaning indicated for formula I. Methanesulfonyl or p-chlorophenylsulfonyl chloride or p-toluenesulfonyl chloride are preferably used.

d) The corticoid-17-alkylcarbonate-21-sulfonic acid esters obtained can optionally be reacted with halide salts in inert solvents according to European Patent No. 0,004,975 to give the corresponding corticoid-17-alkyl-carbonate-21-halides.

For the second process step, the steroid component is dissolved in an inert solvent, for example in an ether, such as dioxane, tetrahydrofuran, diglyme, or optionally halogenated hydrocarbons, such as benzene, toluene, cyclohexane, methylene chloride or chloroform or in a mixture of these solvents. To remove the halohydric acid formed in the reaction, 1–1000 mol equivalents of a tertiary base, such as pyridine, quinoline, triethylamine or dimethylaniline, are added. However, an inorganic base such as sodium hydrogen carbonate or calcium carbonate can also be used to remove the acid. 1–200 mol equivalents, preferably 1–3 mol equivalents, of one of the abovementioned acylating agents, optionally dissolved in one of the abovementioned solvents, is then added dropwise at a temperature of −40° C. up to the boiling point of the solvent used, preferably from 0° C. to 25° C. The reaction mixture is then allowed to stand for one to 120 hours at a temperature of −40° C. up to the boiling point of the solvent, preferably from 0° C. to 25° C.

When using carboxylic anhydrides as acylating agents, it is often advantageous to work without the addition of solvents. As a rule, it is sufficient only to add the organic base, preferably pyridine, to the acid anhydride used in excess.

For working up, the reaction mixture is poured into water to which sodium bicarbonate has optionally been added, whereupon the reaction products are in general obtained in crystalline form, often only after relatively long standing. Oily reaction products which remain are concentrated by shaking with a suitable extracting agent and evaporating. If necessary, the reaction products can be separated or purified by recrystallizing or by chromatography. Often, intensively digesting in an organic solvent dissolving the reaction product as little as possible or not dissolving the reaction product, such as diethyl ether or cyclohexane or a mixture of these components, is also sufficient for the further purification of the reaction products.

A hydroxy group in the 11-position can optionally be oxidized by customary methods to the keto group. Preferably, this oxidation is carried out using chromium trioxide in acid medium and in an inert organic solvent.

The process products have useful pharmacological properties. They have a very strong antiinflammatory activity, in particular locally and topically, and in some cases show a surprisingly good ratio of local to systemic antiinflammatory activity, as can be inferred from pharmacological standard tests.

Accordingly, the invention also relates to an agent for the treatment of inflammatory dermatoses, composed of or containing a compound of the formula I.

The process products can be used in veterinary and human therapy in the form of suspensions, ointments, creams, sprays etc., for the treatment of inflammatory dermatoses of the most diverse origin.

In this case, it is particularly advantageous for the local and topical therapy form to single out the fact that even in the case of high-dosage and long-lasting therapy, it is only possible in practice for the process products to produce minor systemic side effects owing to their very favorable ratio of local to systemic antiinflammatory activity. In the case of external treatment, ointments, creams, suspensions etc. having a concentration of 0.01 to 2% by weight are used. In particular, in pharmacological tests the process products in some cases show a better split (ratio) of local/systemic antiinflammatory activity than corresponding preparations having a linear 17-alkylcarbonate group, which also include the prednicarbate described in European Patent No. 742. Furthermore, the process products in some cases also show a stronger local antiinflammatory activity than their known corticoid analogs having a linearly disposed alkyl moiety in the alkyl radical of the 17-alkylcarbonate groups.

Moreover, corticoid-17-alkylcarbonate-21-derivatives having a branched 17-alkylcarbonate group in the alkyl moiety promise a still lower atrophogenicity compared with analogous corticoid-17-alkylcarbonate-21-derivatives having a linearly disposed 17-alkylcarbonate side chain, which would be a further advantage for a dermatotherapeutic treatment.

Pharmacological test section

Thus, for example, prednisolone-17-isopropylcarbonate-21-acetate (Example 4, fourth compound)=compound I [melting point 126°-128° C.; TLC: $R_F \cong 0.7$], on the one hand showed an about three times stronger local antiinflammatory activity and, on the other hand, also showed a distinctly better split of local/sytemic antiinflammatory activity in comparison to the known (EP 742) isomeric prednisolone-17-n-propylcarbonate-21-acetate=compound II, which can be seen from the pharmacological tests referred to below:

1. Local antiinflammatory action in croton oil ear edema in rats after epicutaneous administration We used the rat ear method of Tonelli et al.: male Wistar rats of our own breeding with a weight of around 50 g were treated epicutaneously on the right ear (20 μl on the inside or outside) with the mixture containing the irritant and/or test substance. The left ear remained untreated. To induce inflammation, in turn, croton oil (C) was used, which was present in the following solvent mixture: C:pyridine: ethanol:ether as 4:20:10:66. The corticoids to be tested were dissolved in this in the final concentrations indicated. Controls received only the C solvent mixture. 4 h after epicutaneous treatment, the animals were anesthetized with ether. Disks measuring 8 mm in diameter were punched out from the right (treated) and the left (untreated) ear and immediately weighed. This difference was set at 100 for controls (mg $\bar{x} \pm s$) as a parameter for the degree of inflammation. The antiinflammatory action is characterized by indication of the approximately 50% inhibitory dose in mg/ml:

Compound I:

| Treatment mg/ml | $\bar{x}$ | $\pm s$ (mg) | Inhibition in % |
|---|---|---|---|
| Control | — | 12.0 | 3.8 | — |
| Compound I | 0.30 | 3.0 | 2.4 | 75% |
| Compound II | 0.30 | 5.0 | 3.6 | 58% |

From this, the fllowing results as an approximately 50% inhibitory dose:

Compound I = 0.1 mg/ml
Compound II = 0.3 mg/ml.

2. Testing for systemic antiinflammatory action in the test "antiinflammatory action after subcutaneous administration: carrageenan paw edema in rats".

Carrageenan paw edema in rats according to the method described by Winter et al. (1962) was selected as a test of the acute systemic antiinflammatory action. Male Sprague-Dawley rats having a weight of around 120 g received the substances to be tested s.c. (0.2 ml/100 g) dissolved in sesame oil. 30 min later, 0.1 to 0.5% carrageenan solution was injected into the left hind paw. 6 h later, the increase in swelling was measured volumetrically. Controls received only sesame oil.

The paw volumes are indicated in ml, $\bar{x} \pm s$. The antiinflammatory action is also characterized here by indication of the approximately 50% inhibitory dose in mg/kg.

| | Dose in mg/kg | Starting value (ml) MW ± S | Vol. increase (ml) after 6 h MW ± S |
|---|---|---|---|
| Control | — | 1.26 ± 0.18 | 0.53 ± 0.14 |
| Compound I | 0.3 | 1.28 ± 0.07 | 0.49 ± 0.23 |
| | 3.0 | 1.34 ± 0.11 | 0.55 ± 0.10 |
| Compound II | 0.3 | 1.25 ± 0.13 | 0.60 ± 0.11 |
| | 3.0 | 13.2 ± 0.10 | 0.13 ± 0.11 |

From this, the following results as an approximately 50% inhibitory dose:

Compound I: >3.0 mg/kg
Compound II: ~0.5 mg/kg

On the basis of the results obtained above from tests 1 and 2, on the one hand an about 3 times stronger local antiinflammatory action of I compared to II and, on the other hand, a reduction of the systemic action of I compared to II by a factor >6 results for the two preparations I and II in the same animal. The split of prednisolone-17-isopropylcarbonate-21-acetate=I compared to prednisolone-17-n-propylcarbonate-21-acetate=II, which is more favorable by an order of magnitude, is clearly documented by means of this. Moreover, the process products according to the invention containing diverse highly skin-compatible locally effective antibiotics, for example of the gentamycin, neomycin, erythromycin, tetracycline or fusidic acid type and others, can be combined in pharmaceutical formulations. Combinations of the process products and the locally effective antibiotics of this type can be used for the treatment of primary bacterial or bacterially reinfected inflammatory dermatoses.

Examples

The general remarks below are to be made for the examples listed in the following:

The melting points are determined in an apparatus according to Tottoli (Büchi) and are uncorrected.

The IR spectra (in KBr) are recorded using the Perkin-Elmer 521 grating spectrophotometer. Only the characteristic bands are indicated in each case. The UV spectra (in methanol) were recorded using the Beckmann DK 1 A spectrophotometer. The mass spectroscopic investigations (MS) are mainly carried out using the MS 9 apparatus (AEI). MS spectra information (molecular weight peak) mainly in:

MS=m/e= . . . (M+H$^+$) (measurement with pure isotopes).

As a rule, FAB-MS spectra were measured.

Ready-to-use silica gel $F_{254}$ plates (Merck) were used for thin layer chromatography (TLC).

If not stated otherwise, methylene chloride: methanol=19:1 was used as the eluant (running distance 7 cm). The plate was in each case developed twice. The spots were detected either using a UV lamp at 254 nm or visualized by spraying with 10% strength methanolic sulfuric acid and by heating to 100° C. The $R_F$ values are always only to be understood as relative. 15 silica gel 60, particle size 0.063-0.2 mm (Merck) was used for column chromatography.

Example 1 a.1.) A solution of 1.2 g of prednisolone-17,21-diisopropylorthocarbonate (TLC:$R_F$ about 0.65) in 18 ml of glacial acetic acid and 0.18 ml of water is allowed to stand at 22° C. for 5 hours. TLC checking showed that after this time an optimum amount of the desired prednisolone-17-isopropylcarbonate was present.

The reaction mixture is poured into 0.5 l of water which had been brought to pH=5 using ammonia solution, whereupon a crystalline precipitate deposited. After filtering off, washing with water and drying, 0.7 g of prednisolone-17-isopropylcarbonate of melting point 128° C. (Tottoli) is obtained after digesting. The remaining aqueous filtrate is extracted using methylene chloride. After distilling off the solvent, a foamy residue remains which is crystallized from diisopropyl ether and gives a further 0.3 g of prednisolone-17-isopropylcarbonate of melting point 126 ° C. Both preparations are combined and recrystallized from ethanol.

Melting point 131° C. (Tottoli) Mass spectrum: MS: m/e=447 (M+H$^+$) TLC: R$_F$≈0.45 (CH$_2$Cl$_2$: CH$_3$OH=19:1) Characterization. IR bands: 3450, 2940, 2870, 1740, 1720, 1270 cm$^{-1}$.

a.2.) It was possible to obtain the same reaction products when the procedure is as follows:

A solution or suspension of 24 g of prednisolone-17,21-diisopropylorthocarbonate in 120 ml of glacial acetic acid and 50 g of ammonium acetate is stirred at 22° C. for 2 hours and, after TLC checking (see a.1.), stirred into 3 l of water saturated with NaCl. The precipiated oil is concentrated after decanting off the aqueous phase through a folded filter and extracted using acid-free methylene chloride. The organic phase is washed with water and dried using sodium sulfate. After distilling off the solvent, 18.5 g of prednisolone-17-isopropylcarbonate is obtained as an oil or foam which, according to TLC (R$_F$ about 0.45), is homogeneous and can be employed in the following reactions without further treatment after drying in a high vacuum.

To give the crystallized preparation, 5 g are crystallized from ethanol/diethyl ether. The same reaction product as described under a.1.) having a melting point of 131° C. and TLC (R$_F$=0.45) is obtained.

b.) In the same manner as described in Example 1) a.2.), 35 g of prednisolone-17,21-diisobutylorthocarbonate are reacted with 73 g of ammonium acetate in 175 ml of glacial acetic acid and the mixture is worked up. 28.4 g of prednisolone-17-isobutylcarbonate are obtained as a foam.

TLC=R$_F$ about 0.5 MS: m/e=461 (M+H$^+$)

c.) In the same manner as described in Example 1.) a.2.), 43 g of prednisolone-17,21-di-tert.-butylmethylorthocarbonate are reacted with 89 g of ammonium acetate in 201 ml of glacial acetic acid and the mixture is worked up. The oily reaction product (34 g) is purified by chromatography on silica gel 35–70 (column dimension 5.5×41 cm). After 3 l of methylene chloride/methanol=89:2 have been passed through (by products according to TLC), 1.5 l of eluant methylene chloride/methanol=96:4 are passed through.

After distilling off the solvent, the desired prednisolone-17-tert.-butylmethylcarbonate is obtained as a pale oil.

TLC about 0.5 MS: m/e=475 (M+H$^+$)

d.) In a similar manner to that described in Example 1) a.2), 21 g of prednisolone-17,21-dimethoxyethylorthocarbonate are stirred at 35°–40° C. in 105 ml of glacial acetic acid and 44 g of ammonium acetate for 4 hours and the mixture is worked up. The oily reaction product obtained (13.5 g) is crystallized from diethyl ether and gives 8.2 g of prednisolone-17-methoxyethylcarbonate of melting point 131° C.

MS: m/e=463 (M+H$^+$)

Example 2 a.) 35 ml of acetic anhydride are added to a solution of 6 g of prednisolone-17-isobutylcarbonate in 55 ml of pyridine. After stirring at 20° C. for 4 hours, the mixture is stirred into 1.8 l of half-saturated aqueous sodium chloride solution, whereupon an oil precipitates. The aqueous phase is decanted off, the oil is taken up using methylene chloride, and the organic phase is washed with water and dried using sodium sulfate. After distilling off the solvent, an oil remains which is crystallized from diethyl ether. 3.5 g of crystallized prednisolone-17-isobutylcarbonate-21-acetate are obtained of melting point 185° C., MS: m/e 503 (M+H$^+$)

b.) 2 g of highest purity propionyl chloride in 2 ml of dioxane are added dropwise with stirring and at 0° C. in the course of 60 min to a solution of 6.85 g of prednisolone-17-isobutylcarbonate in 68 ml of absol. pyridine. After stirring at 0° C. for 30 minutes and at 20° C. for 3 hours, the reaction mixture is poured into 1.8 l of water which contains 100 g of NaCl. The oily precipitate is filtered off, washed well with water and dried in a high vacuum. 6.3 g of foam are obtained, which, in the TLC, in addition to the main spot at R$_F$=0.7, also contains weak secondary spots at R$_F$ about 0.5–0.55. For preparation in pure form, the product is chromatographed on 150 g of silica gel (particle size 0.063–0.200 mm (Merck AG); column 28×5 cm) using 1.7 l of methylene chloride and 800 ml of methylene chloride/methanol=995:5. After distilling off the eluant, 3.8 g of crystallized prednisolone-17-isobutyl-carbonate-21-n-propionate of melting point 136° C. are obtained from diethyl ether MS: m/e=571 (M+H$^+$)

TLC: R$_F$≈0.7

Example 3

The corticosteroid-17-alkylcarbonates of the formula I having a free 21-hydroxy group (R(1)=OH) shown in Table 1 are obtained from the corticosteroid-17,21-orthoalkylcarbonates of the formula V in the same manner as described in Example 1 a.1.) or a.2.):

TABLE 1

| Basic cortiscosteriod | Process variant (Ex. 1) | A | Y | Z | R(2) | R(3) | Mass spectrum (m/e) M + H$^+$ | TLC: R$_F$ |
|---|---|---|---|---|---|---|---|---|
| Dexamethasone | a.2.) | CHOH | F | H | —CH(CH$_3$)$_2$ | CH$_3$ | 479 | 0.55 |
| " | " | " | " | " | —CH$_2$CH(CH$_3$)$_2$ | " | 493 | 0.55 |
| " | " | " | " | " | —CH$_2$C(CH$_3$)$_3$ | " | 507 | 0.55 |
| " | " | " | " | " | —CH$_2$CH$_2$OCH$_3$ | " | 495 | 0.5 |
| 6α-Methylprednisolone | a.2.) | CHOH | H | CH$_3$ | —CH(CH$_3$)$_2$ | H | 461 | |
| " | " | " | " | " | —CH$_2$CH(CH$_3$)$_2$ | " | 475.4 | 0.5 |
| " | " | " | " | " | —CH$_2$C(CH$_3$)$_3$ | " | 489 | 0.5 |
| " | " | " | " | " | —CH$_2$CH$_2$OCH$_3$ | " | 477 | |
| 6α-Fluorodexamethasone | a.2.) | CHOH | F | F | —CH(CH$_3$)$_2$ | CH$_3$ | 497 | 0.5 |

TABLE 1-continued

| Basic cortiscosteriod | Process variant (Ex. 1) | A | Y | Z | R(2) | R(3) | Mass spectrum (m/e) M + H$^+$ | TLC: R$_F$ |
|---|---|---|---|---|---|---|---|---|
| " | " | " | " | " | —CH$_2$CH(CH$_3$)$_2$ | " | 511 | |
| 6α-Fluorodexamethasone | " | " | " | " | —CH$_2$C(CH$_3$)$_3$ | " | 525 | |
| " | " | " | " | " | —CH$_2$CH$_2$OCH$_3$ | " | 513 | |
| Cortisol (1,2,-dihydro) | a.2.) | CHOH | H | H | —CH(CH$_3$)$_2$ | H | 449 | |
| " | " | " | " | " | —CH$_2$CH(CH$_3$)$_2$ | H | 463 | 0.5 |
| Cortisone (1,2-dihydro) | a.2.) | C═O | H | H | —CH(CH$_3$)$_2$ | H | 447 | |
| " | a.1.) | " | " | " | —CH$_2$CH(CH$_3$)$_2$ | H | 461 | |
| Cortisol | " | " | " | " | —CH$_2$C(CH$_3$)$_3$ | " | 477 | |
| " | " | " | " | " | —CH$_2$CH$_2$OCH$_3$ | " | 465 | |
| Prednisone | a.2.) | C═O | H | H | —CH(CH$_3$)$_2$ | H | 445 | 0.5 |
| " | " | " | " | H | —CH$_2$CH(CH$_3$)$_2$ | H | 459 | |
| " | " | " | " | " | —CH$_2$C(CH$_3$)$_3$ | " | 473 | |
| " | " | " | " | " | —CH$_2$CH$_2$OCH$_3$ | " | 461 | |
| 6α-Fluoroprednisolone | a.2.) | CHOH | H | F | —CH$_2$CH(CH$_3$)$_2$ | H | 479 | 0.55 |
| 6α,16α-Dimethyl-prednisolone | a.2.) | CHOH | H | CH$_3$ | —CH$_2$CH(CH$_3$)$_2$ | CH$_3$ | 489 | |
| Reichstein's substance S | a.2.) | —CH$_2$— | H | H | —CH$_2$CH(CH$_3$)$_2$ | H | 477 | 0.6 |
| " | " | " | " | " | —CH(CH$_3$)$_2$ | H | 433 | |

Example 4

In the same manner, the following are obtained from Prednisolone-17-isopropoylcarbonate, from prednisolone-17-tert.-butylmethylcarbonate and from prednisolone-17-methoxyethylcarbonate if 1.) the procedure is as in Example 2, b.):

Prednisolone-17-isopropylcarbonate-21-propionate
  MS=m/e=503 (M+H$^+$)
Prednisolone-17-tert.-butylmethylcarbonate-21-propionate
  MS=m/e 531 (M+H$^+$)
Prednisolone-17-methoxyethylcarbonate-21-propionate
  MS=m/e 519 (M+H$^+$) if 2.) the procedure is as in Example 2,a.):
Prednisolone-17-isopropylcarbonate-21-acetate
  MS=m/e 489 (M+H$^+$)
Prednisolone-17-tert.-butylmethylcarbonate-21-acetate
  MS=m/e 505(M+H$^+$)
prednisolone-17-methoxyethylcarbonate-21-acetate
  MS=m/e 4505(M+H$^+$)

Example 5

In the same or a similar manner to that described in Example 2.a.) and 2.b.), the following corticosteroid-17-alkylcarbonate-21-carboxylic acid esters (R(1)=OCO(CH$_2$)$_n$—R(4)), -21-carbonic acid esters (R(1)=OCO$_2$(CH$_2$)$_n$—R(4)) or 21-alkyl- or arylsulfonic acid esters (R(1)=OSO$_2$R(5)) of the formula I as in Tables 2–7 are prepared or obtained if, instead of acetic anhydride, the analogous carboxylic acid anhydrides (CO[CO(CH$_2$)$_n$R(4)]$_2$) are employed in Example 2.a.) or, instead of propionyl chloride, the corresponding carboxylic acid chlorides (Cl—CO—(CH$_2$)$_n$R(4)) or carbonic acid chlorides or chloroformic acid esters (Cl—CO—O—(CH$_2$)$_n$R(4)) or alkyl- or arylsulfonyl chlorides (Cl—SO$_2$—R(5)) are employed in Example 2.b.).

The meanings o f A, Y, Z, R(3), R(2), R(1), R(4) and R( 5) are indicated at the beginning for formula I.

Note

In the corresponding reactions with alkyl- or arylsulfonyl chlorides, absolute acetone is advantageously added to the reaction mixture, the ratio of acetone/pyridine being about 10:4.

In the reactions with carboxylic acid chlorides, absolute dioxane is advantageously often added to the reaction mixture, for example in the case of cyclopropylcarbonyl chloride, where the ratio dioxane/pyridine is about 1:1, and to accelerate the reaction the reaction mixture is often heated, in particular in the case of cyclopropylcarbonyl chloride, to about 60° C. (TLC monitoring of the reaction courses).

The characterization of the reaction products can be carried out by thin layer chromatography (TLC); in this case the reaction products have R$_F$ values of about 0.65–0.75. As a rule, the reaction products are characterized by mass spectra with MS=m/e= ... (M+H$^+$) (as a rule FAB spectra).

The M+H$^+$ values were in each case rounded up. IR, $^1$H-NMR and UV spectra can also be used for characterization.

TABLE 2a

| | | | Basic corticoid = Prednisolone (Pred.) | | | | | | |
|---|---|---|---|---|---|---|---|---|---|
| Reagent: (anhydride or chloride) | Basic corticoid | Process variant Example 2 | A | Y | Z | R(3) | R(2) | R(1) | MS (m/e) M + H$^+$ |
| CH$_3$(CH$_2$)$_2$COCl | Pred. | 2.b.) | CHOH | H | H | H | —CH(CH$_3$)$_2$ | OCO(CH$_2$)$_2$CH$_3$ | 517 |
| CH$_3$(CH$_2$)$_3$COCl | " | " | " | " | " | " | " | OCO(CH$_2$)$_3$CH$_3$ | 531 |
| CH$_3$(CH$_2$)$_4$COCl | " | " | " | " | " | " | " | OCO(CH$_2$)$_4$CH$_3$ | 545 |
| (CH$_3$)$_2$CHCOCl | " | " | " | " | " | " | " | OCOCH(CH$_3$)$_2$ | 517 |
| (CH$_3$)$_3$CCOCl | " | " | " | " | " | " | " | OCOC(CH$_3$)$_3$ | 531 |
| 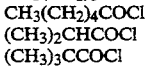 | " | " | " | " | " | " | " | 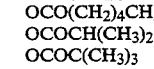 | 515 |

TABLE 2a-continued

| | Basic corticoid = Prednisolone (Pred.) | | | | | | | |
|---|---|---|---|---|---|---|---|---|
| Reagent: (anhydride or chloride) | Basic corticoid | Process variant Example 2 | A | Y | Z | R(3) | R(2) | R(1) | MS (m/e) M + H+ |

| Reagent | Basic corticoid | Process variant | A | Y | Z | R(3) | R(2) | R(1) | MS M+H+ |
|---|---|---|---|---|---|---|---|---|---|
| 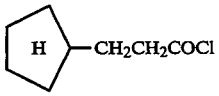—CH₂CH₂COCl | " | " | " | " | " | " | " | OCOCH₂CH₂—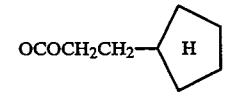 | 571 |
| CH₃OCO—Cl | " | " | " | " | " | " | " | OCO₂CH₃ | 505 |
| C₂H₅OCO—Cl | " | " | " | " | " | " | " | OCO₂C₂H₅ | 519 |
| C₃H₇—OCO—Cl | " | " | " | " | " | " | " | OCO₂C₃H₇ | 533 |
| CH₃SO₂—Cl | " | " | " | " | " | " | " | OSO₂CH₃ | 529 |
| C₆H₅SO₂—Cl | " | " | " | " | " | " | " | OSO₂C₆H₅ | 587 |
| p-Cl—C₆H₄—SO₂—Cl | " | " | " | " | " | " | " | OSO₂—C₆H₄-p-Cl | 622 |
| p-CH₃—C₆H₄—SO₂—Cl (p-Tosylchloride) | " | " | " | " | " | " | " | OSO₂—C₆H₄-p-CH₃ | 601 |

TABLE 2b

| | Basic corticoid = Prednisolone (Pred.) | | | | | | | |
|---|---|---|---|---|---|---|---|---|

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| CH₃(CH₂)₂COCl | Pred. | 2.b.) | CHOH | H | H | H | —CH₂CH(CH₃)₂ | OCO(CH₂)₂CH₃ | 531 |
| CH₃(CH₂)₃COCl | " | " | " | " | " | " | " | OCO(CH₂)₃CH₃ | 545 |
| CH₃(CH₂)₄COCl | " | " | " | " | " | " | " | OCO(CH₂)₄CH₃ | 559 |
| (CH₃)₂CHCOCl | " | " | " | " | " | " | " | OCOCH(CH₃)₂ | 531 |
| (CH₃)₃CCOCl | " | " | " | " | " | " | " | OCOC(CH₃)₃ | 545 |
| 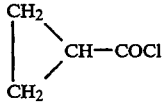 | " | " | " | " | " | " | " | 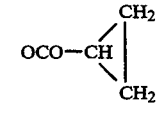 | 529 |
| 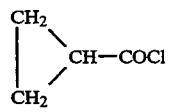—CH₂CH₂COCl | " | " | " | " | " | " | " | OCOCH₂CH₂—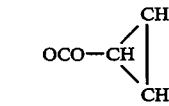 | 585 |
| CH₃OCO—Cl | " | " | " | " | " | " | " | OCO₂CH₃ | 519 |
| C₂H₅OCO—Cl | " | " | " | " | " | " | " | OCO₂C₂H₅ | 533 |
| C₃H₇—OCO—Cl | " | " | " | " | " | " | " | OCO₂C₃H₇ | 547 |
| CH₃SO₂—Cl | " | " | " | " | " | " | " | OSO₂CH₃ | 539 |
| C₆H₅SO₂—Cl | " | " | " | " | " | " | " | OSO₂C₆H₅ | 601 |
| p-Cl—C₆H₄—SO₂—Cl | " | " | " | " | " | " | " | OSO₂—C₆H₄-p-Cl | 636 |
| p-CH₃—C₆H₄—SO₂—Cl (p-Tosylchloride) | " | " | " | " | " | " | " | OSO₂—C₆H₄-p-CH₃ | 615 |

TABLE 2c

| | Basic corticoid = Prednisolone (Pred.) | | | | | | | |
|---|---|---|---|---|---|---|---|---|

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| CH₃(CH₂)₂COCl | Pred. | 2.b.) | CHOH | H | H | H | —CH₂C(CH₃)₃ | OCO(CH₂)₂CH₃ | 545 |
| CH₃(CH₂)₃COCl | " | " | " | " | " | " | " | OCO(CH₂)₃CH₃ | 559 |
| CH₃(CH₂)₄COCl | " | " | " | " | " | " | " | OCO(CH₂)₄CH₃ | 573 |
| (CH₃)₂CHCOCl | " | " | " | " | " | " | " | OCOCH(CH₃)₂ | 545 |
| (CH₃)₃CCOCl | " | " | " | " | " | " | " | OCOC(CH₃)₃ | 559 |
| (cyclopropyl-COCl) | " | " | " | " | " | " | " | OCO—(cyclopropyl) | 543 |
| C₂H₅OCO—Cl | " | " | " | " | " | " | " | OCO₂C₂H₅ | 547 |
| CH₃SO₂—Cl | " | " | " | " | " | " | " | OSO₂CH₃ | 553 |
| p-Cl—C₆H₄—SO₂—Cl | " | " | " | " | " | " | " | OSO₂—C₆H₄-p-Cl | 650 |

TABLE 2d

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| Basic corticoid = Prednisolone (Pred.) ||||||||||
| CH₃(CH₂)₂COCl | Pred. | 2.b.) | CHOH | H | H | H | —CH₂CH₂OCH₃ | OCO(CH₂)₂CH₃ | 533 |
| CH₃(CH₂)₃COCl | " | " | " | " | " | " | " | OCO(CH₂)₃CH₃ | 547 |
| (CH₃)₂CHCOCl | " | " | " | " | " | " | " | OCOCH(CH₃)₂ | 533 |
| CH₂\CH—COCl/CH₂ | " | " | " | " | " | " | " | OCO—CH(CH₂\CH₂) | 531 |
| C₂H₅OCO—Cl | " | " | " | " | " | " | " | OCO₂C₂H₅ | 535 |
| CH₃SO₂—Cl | " | " | " | " | " | " | " | OSO₂CH₃ | 545 |
| p-Cl—C₆H₄—SO₂—Cl | " | " | " | " | " | " | " | OSO₂—C₆H₄-p-Cl | 638 |

TABLE 3a

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| Basic corticoid = Dexamethasone (Dex.) ||||||||||
| (CH₃CO)₂O | Dex. | 2.a.) | CHOH | F | H | CH₃ | —CH(CH₃)₂ | OCOCH₃ | 521 |
| CH₃CH₂COCl | " | 2.b.) | " | " | " | " | " | OCOC₂H₅ | 535 |
| CH₃(CH₂)₂COCl | " | " | " | " | " | " | " | OCO(CH₂)₂CH₃ | 549 |
| CH₃(CH₂)₃COCl | " | " | " | " | " | " | " | OCO(CH₂)₃CH₃ | 563 |
| CH₃(CH₂)₄COCl | " | " | " | " | " | " | " | OCO(CH₂)₄CH₃ | 577 |
| (CH₃)₂CHCOCl | " | " | " | " | " | " | " | OCOCH(CH₃)₂ | 549 |
| (CH₃)₃CCOCl | " | " | " | " | " | " | " | OCOC(CH₃)₃ | 563 |
| CH₂\CH—COCl/CH₂ | " | " | " | " | " | " | " | OCO—CH(CH₂\CH₂) | 547 |
| ⬠H—CH₂CH₂COCl | " | " | " | " | " | " | " | OCOCH₂CH₂—H | 603 |
| CH₃OCO—Cl | " | " | " | " | " | " | " | OCO₂CH₃ | 537 |
| C₂H₅OCO—Cl | " | " | " | " | " | " | " | OCO₂C₂H₅ | 551 |
| C₃H₇—OCO—Cl | " | " | " | " | " | " | " | OCO₂C₃H₇ | 565 |
| CH₃SO₂—Cl | " | " | " | " | " | " | " | OSO₂CH₃ | 561 |
| p-Cl—C₆H₄—SO₂—Cl | " | " | " | " | " | " | " | OSO₂—C₆H₄-p-Cl | 654 |
| p-CH₃—C₆H₄—SO₂—Cl (p-Tosylchloride) | " | " | " | " | " | " | " | OSO₂—C₆H₄-p-CH₃ | 633 |

TABLE 3b

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| Basic corticoid = Dexamethasone (Dex.) ||||||||||
| (CH₃CO)₂O | Dex. | 2.a.) | CHOH | F | H | CH₃ | —CH₂CH(CH₃)₂ | OCOCH₃ | 535 |
| CH₃CH₂COCl | " | 2.b.) | " | " | " | " | " | OCOC₂H₅ | 549 |
| CH₃(CH₂)₂COCl | " | " | " | " | " | " | " | OCO(CH₂)₂CH₃ | 563 |
| CH₃(CH₂)₃COCl | " | " | " | " | " | " | " | OCO(CH₂)₃CH₃ | 577 |
| CH₃(CH₂)₄COCl | " | " | " | " | " | " | " | OCO(CH₂)₄CH₃ | 591 |
| (CH₃)₂CHCOCl | " | " | " | " | " | " | " | OCOCH(CH₃)₂ | 563 |
| (CH₃)₃CCOCl | " | " | " | " | " | " | " | OCOC(CH₃)₃ | 577 |
| CH₂\CH—COCl/CH₂ | " | " | " | " | " | " | " | OCO—CH(CH₂\CH₂) | 561 |
| ⬠H—CH₂CH₂COCl | " | " | " | " | " | " | " | OCOCH₂CH₂—H | 617 |

TABLE 3b-continued

Basic corticoid = Dexamethasone (Dex.)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| CH₃OCO—Cl | " | " | " | " | " | " | " | OCO₂CH₃ | 551 |
| C₂H₅OCO—Cl | " | " | " | " | " | " | " | OCO₂C₂H₅ | 565 |
| C₃H₇—OCO—Cl | " | " | " | " | " | " | " | OCO₂C₃H₇ | 579 |
| CH₃SO₂—Cl | " | " | " | " | " | " | " | OSO₂CH₃ | 571 |
| C₆H₅—SO₂—Cl | " | " | " | " | " | " | " | OSO₂C₆H₅ | 633 |
| p-Cl—C₆H₄—SO₂—Cl | " | " | " | " | " | " | " | OSO₂—C₆H₄-p-Cl | 668 |
| p-CH₃—C₆H₄—SO₂—Cl (p-Tosylchloride) | " | " | " | " | " | " | " | OSO₂—C₆H₄-p-CH₃ | 647 |

TABLE 3c

Basic corticoid = Dexamethasone (Dex.)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH₃CO)₂O | Dex. | 2.a.) | CHOH | F | H | CH₃ | —CH₂C(CH₃)₃ | OCOCH₃ | 549 |
| CH₃CH₂COCl | " | 2.b.) | " | " | " | " | " | OCOC₂H₅ | 563 |
| CH₃(CH₂)₂COCl | " | " | " | " | " | " | " | OCO(CH₂)₂CH₃ | 577 |
| (CH₃)₂CHCOCl | " | " | " | " | " | " | " | OCOCH(CH₃)₂ | 577 |
| CH₂\|CH—COCl / CH₂ (cyclopropyl) | " | " | " | " | " | " | " | OCO—CH(cyclopropyl) | 575 |
| C₂H₅OCO—Cl | " | " | " | " | " | " | " | OCO₂C₂H₅ | 579 |
| CH₃SO₂—Cl | " | " | " | " | " | " | " | OSO₂CH₃ | 585 |
| p-Cl—C₆H₄—SO₂—Cl | " | " | " | " | " | " | " | OSO₂—C₆H₄-p-Cl | 682 |

TABLE 3d

Basic corticoid = Dexamethasone (Dex.)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH₃CO)₂O | Dex. | 2.a.) | CHOH | F | H | CH₃ | —CH₂CH₂OCH₃ | OCOCH₃ | 537 |
| CH₃CH₂COCl | " | 2.b.) | " | " | " | " | " | OCOC₂H₅ | 551 |
| CH₃(CH₂)₂COCl | " | " | " | " | " | " | " | OCO(CH₂)₂CH₃ | 565 |
| (CH₃)₂CHCOCl | " | " | " | " | " | " | " | OCOCH(CH₃)₂ | 565 |
| (CH₃)₃CCOCl | " | " | " | " | " | " | " | OCOC(CH₃)₃ | 579 |
| CH₂\|CH—COCl / CH₂ (cyclopropyl) | " | " | " | " | " | " | " | OCO—CH(cyclopropyl) | 563 |
| C₂H₅OCO—Cl | " | " | " | " | " | " | " | OCO₂C₂H₅ | 567 |
| CH₃SO₂—Cl | " | " | " | " | " | " | " | OSO₂CH₃ | 577 |
| p-Cl—C₆H₄—SO₂—Cl | " | " | " | " | " | " | " | OSO₂—C₆H₄-p-Cl | 670 |

TABLE 4a

Basic corticoid = 6α-Methylprednisolone (M-pred.)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH₃CO)₂O | M.pred. | 2.a.) | CHOH | H | CH₃ | H | —CH(CH₃)₂ | OCOCH₃ | 503 |
| CH₃CH₂COCl | " | 2.b.) | " | " | " | " | " | OCOC₂H₅ | 517 |
| CH₃(CH₂)₂COCl | " | " | " | " | " | " | " | OCO(CH₂)₂CH₃ | 531 |
| (CH₃)₂CHCOCl | " | " | " | " | " | " | " | OCOCH(CH₃)₂ | 531 |
| (CH₃)₃CCOCl | " | " | " | " | " | " | " | OCOC(CH₃)₃ | 545 |
| CH₂\|CH—COCl / CH₂ (cyclopropyl) | " | " | " | " | " | " | " | OCO—CH(cyclopropyl) | 529 |
| C₂H₅OCO—Cl | " | " | " | " | " | " | " | OCO₂C₂H₅ | 533 |
| CH₃SO₂—Cl | " | " | " | " | " | " | " | OSO₂CH₃ | 543 |

TABLE 4a-continued

Basic corticoid = 6α-Methylprednisolone (M-pred.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| p-Cl—C₆H₄—SO₂—Cl | " | " | " | " | " | " | " | OSO₂—C₆H₄-p-Cl | 636 |

TABLE 4b

Basic corticoid = 6α-Methylprednisolone (M-pred.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | M.pred. | 2.a.) | CHOH | H | CH₃ | H | —CH₂CH(CH₃)₂ | OCOCH₃ | 517 |
| CH₃CH₂COCl | " | 2.b.) | " | " | " | " | " | OCOC₂H₅ | 531 |
| CH₃(CH₂)₂COCl | " | " | " | " | " | " | " | OCO(CH₂)₂CH₃ | 545 |
| CH₃(CH₂)₃COCl | " | " | " | " | " | " | " | OCO(CH₂)₃CH₃ | 559 |
| (CH₃)₂CHCOCl | " | " | " | " | " | " | " | OCOCH(CH₃)₂ | 545 |
| (CH₃)₃CCOCl | " | " | " | " | " | " | " | OCOC(CH₃)₃ | 559 |
| cyclopropyl-COCl | " | " | " | " | " | " | " | OCO-cyclopropyl | 543 |
| cyclopentyl-CH₂CH₂COCl | " | " | " | " | " | " | " | OCOCH₂CH₂-cyclopentyl | 599 |
| C₂H₅OCO—Cl | " | " | " | " | " | " | " | OCO₂C₂H₅ | 547 |
| C₃H₇—OCO—Cl | " | " | " | " | " | " | " | OCO₂C₃H₇ | 561 |
| CH₃SO₂—Cl | " | " | " | " | " | " | " | OSO₂CH₃ | 553 |
| p-Cl—C₆H₄—SO₂—Cl | " | " | " | " | " | " | " | OSO₂—C₆H₄-p-Cl | 650 |
| p-CH₃—C₆H₄—SO₂—Cl (p-Tosylchloride) | " | " | " | " | " | " | " | OSO₂—C₆H₄-p-CH₃ | 629 |

TABLE 4c

Basic corticoid = 6α-Methylprednisolone (M-pred.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | M.pred. | 2.a.) | CHOH | H | CH₃ | H | —CH₂C(CH₃)₃ | OCOCH₃ | 531 |
| CH₃CH₂COCl | " | 2.b.) | " | " | " | " | " | OCOC₂H₅ | 545 |
| (CH₃)₂CHCOCl | " | " | " | " | " | " | " | OCOCH(CH₃)₂ | 559 |
| (CH₃)₃CCOCl | " | " | " | " | " | " | " | OCOC(CH₃)₃ | 573 |
| cyclopropyl-COCl | " | " | " | " | " | " | " | OCO-cyclopropyl | 557 |
| C₂H₅OCO—Cl | " | " | " | " | " | " | " | OCO₂C₂H₅ | 561 |
| CH₃SO₂—Cl | " | " | " | " | " | " | " | OSO₂CH₃ | 567 |
| p-Cl—C₆H₄—SO₂—Cl | " | " | " | " | " | " | " | OSO₂—C₆H₄-p-Cl | 664 |

TABLE 4d

Basic corticoid = Dexamethasone (Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | M.pred. | 2.a.) | CHOH | H | CH₃ | H | CH₂CH₂OCH₃ | OCOCH₃ | 519 |
| CH₃CH₂COCl | " | 2.b.) | " | " | " | " | " | OCOC₂H₅ | 533 |
| CH₃(CH₂)₂COCl | " | " | " | " | " | " | " | OCO(CH₂)₂CH₃ | 547 |
| cyclopropyl-COCl | " | " | " | " | " | " | " | OCO-cyclopropyl | 545 |
| C₂H₅OCO—Cl | " | " | " | " | " | " | " | OCO₂C₂H₅ | 549 |

TABLE 4d-continued

Basic corticoid = Dexamethasone (Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| CH₃SO₂—Cl | " | " | " | " | " | " | " | OSO₂CH₃ | 559 |
| p-Cl—C₆H₄—SO₂—Cl | " | " | " | " | " | " | " | OSO₂—C₆H₄-p-Cl | 652 |

TABLE 5a

Basic corticoid = 6α-Fluorodexamethasone (F.-Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | F-Dex. | 2.a.) | CHOH | F | F | CH₃ | —CH(CH₃)₂ | OCOCH₃ | 539 |
| CH₃CH₂COCl | " | 2.b.) | " | " | " | " | " | OCOC₂H₅ | 553 |
| CH₃(CH₂)₂COCl | " | " | " | " | " | " | " | OCO(CH₂)₂CH₃ | 567 |
| CH₃(CH₂)₃COCl | " | " | " | " | " | " | " | OCO(CH₂)₃CH₃ | 581 |
| (CH₃)₂CHCOCl | " | " | " | " | " | " | " | OCOCH(CH₃)₂ | 567 |
| 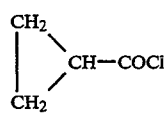 | " | " | " | " | " | " | " | 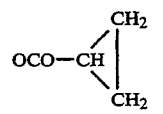 | 565 |
| C₂H₅OCO—Cl | " | " | " | " | " | " | " | OCO₂C₂H₅ | 569 |
| CH₃SO₂—Cl | " | " | " | " | " | " | " | OSO₂CH₃ | 579 |
| p-Cl—C₆H₄—SO₂—Cl | " | " | " | " | " | " | " | OSO₂—C₆H₄-p-Cl | 672 |

TABLE 5b

Basic corticoid = 6α-Fluorodexamethasone (F.-Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | F-Dex. | 2.a.) | CHOH | F | F | CH₃ | —CH₂CH(CH₃)₂ | OCOCH₃ | 553 |
| CH₃CH₂COCl | " | 2.b.) | " | " | " | " | " | OCOC₂H₅ | 567 |
| CH₃(CH₂)₂COCl | " | " | " | " | " | " | " | OCO(CH₂)₂CH₃ | 581 |
| CH₃(CH₂)₃COCl | " | " | " | " | " | " | " | OCO(CH₂)₃CH₃ | 595 |
| (CH₃)₂CHCOCl | " | " | " | " | " | " | " | OCOCH(CH₃)₂ | 581 |
| 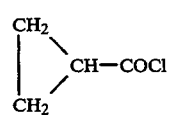 | " | " | " | " | " | " | " | 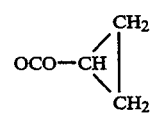 | 579 |
| C₂H₅OCO—Cl | " | " | " | " | " | " | " | OCO₂C₂H₅ | 583 |
| CH₃SO₂—Cl | " | " | " | " | " | " | " | OSO₂CH₃ | 589 |
| p-Cl—C₆H₄—SO₂—Cl | " | " | " | " | " | " | " | OSO₂—C₆H₄-p-Cl | 686 |

TABLE 5c

Basic corticoid = 6α-Fluorodexamethasone (F.-Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | F-Dex. | 2.a.) | CHOH | F | F | CH₃ | —CH₂C(CH₃)₃ | OCOCH₃ | 567 |
| CH₃CH₂COCl | " | 2.b.) | " | " | " | " | " | OCOC₂H₅ | 581 |
| p-Cl—C₆H₄—SO₂—Cl | " | " | " | " | " | " | " | OSO₂—C₆H₄-p-Cl | 700 |

TABLE 5d

Basic corticoid = 6α-Fluorodexamethasone (F.-Dex.)

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | F-Dex. | 2.a.) | CHOH | F | F | CH₃ | CH₂CH₂OCH₃ | OCOCH₃ | 555 |
| CH₃CH₂COCl | " | 2.b.) | " | " | " | " | " | OCOC₂H₅ | 569 |
| CH₃(CH₂)₂COCl | " | " | " | " | " | " | " | OCO(CH₂)₂CH₃ | 583 |

TABLE 5d-continued

| | Basic corticoid = 6α-Fluorodexamethasone (F.-Dex.) | | | | | | | MS (m/e) |
|---|---|---|---|---|---|---|---|---|
| Reagent: (anhydride or chloride) | Basic corticoid | Process variant Example 2 | A | Y | Z | R(3) | R(2) | R(1) | M + H⁺ |

| Reagent | Basic corticoid | Ex.2 | A | Y | Z | R(3) | R(2) | R(1) | MS |
|---|---|---|---|---|---|---|---|---|---|
| 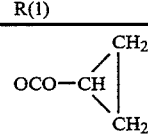 (cyclopropyl-COCl) | " | " | " | " | " | " | " | OCO—CH(CH₂)₂ (cyclopropyl) | 581 |
| C₂H₅OCO—Cl | " | " | " | " | " | " | " | OCO₂C₂H₅ | 585 |
| p-Cl—C₆H₄—SO₂—Cl | " | " | " | " | " | " | " | OSO₂—C₆H₄-p-Cl | 688 |

TABLE 6a

Basic corticoid = Cortisol (Cort.) (in 1,2-pos.: 1,2-dihydro)

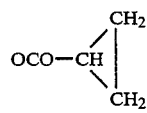

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | Cort. | 2.a.) | CHOH | H | H | H | —CH(CH₃)₂ | OCOCH₃ | 491 |
| CH₃CH₂COCl | " | 2.b.) | " | " | " | " | " | OCOC₂H₅ | 505 |
| CH₃(CH₂)₂COCl | " | " | " | " | " | " | " | OCO(CH₂)₂CH₃ | 519 |
| CH₃(CH₂)₃COCl | " | " | " | " | " | " | " | OCO(CH₂)₃CH₃ | 533 |
| (CH₃)₂CHCOCl | " | " | " | " | " | " | " | OCOCH(CH₃)₂ | 519 |
| cyclopropyl-COCl | " | " | " | " | " | " | " | OCO—cyclopropyl | 517 |
| cyclopentyl-CH₂CH₂COCl | " | " | " | " | " | " | " | OCOCH₂CH₂-cyclopentyl | 573 |
| C₂H₅OCO—Cl | " | " | " | " | " | " | " | OCO₂C₂H₅ | 521 |
| CH₃SO₂—Cl | " | " | " | " | " | " | " | OSO₂CH₃ | 531 |
| p-Cl—C₆H₄—SO₂—Cl | " | " | " | " | " | " | " | OSO₂—C₆H₄-p-Cl | 624 |

TABLE 6b

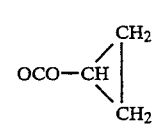

| Reagent: (anhydride or chloride) | Basic corticoid | Process variant Example 2 | A | Y | Z | R(3) | R(2) | R(1) | MS (m/e) M + H⁺ |
|---|---|---|---|---|---|---|---|---|---|
| (CH₃CO)₂O | Cort. | 2.a.) | CHOH | H | H | H | —CH₂CH(CH₃)₂ | OCOCH₃ | 505 |
| CH₃CH₂COCl | " | 2.b.) | " | " | " | " | " | OCOC₂H₅ | 519 |
| CH₃(CH₂)₂COCl | " | " | " | " | " | " | " | OCO(CH₂)₂CH₃ | 533 |
| CH₃(CH₂)₃COCl | " | " | " | " | " | " | " | OCO(CH₂)₃CH₃ | 547 |
| (CH₃)₂CHCOCl | " | " | " | " | " | " | " | OCOCH(CH₃)₂ | 533 |
| cyclopropyl-COCl | " | " | " | " | " | " | " | OCO—cyclopropyl | 531 |
| C₂H₅OCO—Cl | " | " | " | " | " | " | " | OCO₂C₂H₅ | 535 |
| CH₃SO₂—Cl | " | " | " | " | " | " | " | OSO₂CH₃ | 541 |
| p-Cl—C₆H₄—SO₂—Cl | " | " | " | " | " | " | " | OSO₂—C₆H₄-p-Cl | 638 |

TABLE 6c

| | Basic corticoid = Cortisol (Cort.) | | | | | | | | |
|---|---|---|---|---|---|---|---|---|---|
| Reagent: (anhydride or chloride) | Basic corticoid | Process variant Example 2 | A | Y | Z | R(3) | R(2) | R(1) | MS (m/e) M + H⁺ |
| (CH₃CO)₂O | Cort. | 2.a.) | CHOH | H | H | H | —CH₂C(CH₃)₃ | OCOCH₃ | 519 |
| CH₃CH₂COCl | " | 2.b.) | " | " | " | " | " | OCOC₂H₅ | 533 |
| p-Cl—C₆H₄—SO₂—Cl | " | " | " | " | " | " | " | OSO₂—C₆H₄-p-Cl | 652 |

TABLE 6d

Basic corticoid = Cortisol (Cort.)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH3CO)2O | Cort. | 2.a.) | CHOH | H | H | H | CH2CH2OCH3 | OCOCH3 | 507 |
| CH3CH2COCl | " | 2.b.) | " | " | " | " | " | OCOC2H5 | 521 |
| CH3(CH2)2COCl | " | " | " | " | " | " | " | OCO(CH2)2CH3 | 535 |
| CH2<br>  \<br>   CH—COCl<br>  /<br>CH2 | " | " | " | " | " | " | " | OCO—CH(CH2/CH2) | 533 |
| C2H5OCO—Cl | " | " | " | " | " | " | " | OCO2C2H5 | 537 |
| p-Cl—C6H4—SO2—Cl | " | " | " | " | " | " | " | OSO2—C6H4-p-Cl | 640 |

TABLE 7a

Basic corticoid = Prednisone (Pre-n)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH3CO)2O | Pre-n | 2.a.) | C=O | H | H | H | —CH2CH(CH3)2 | OCOCH3 | 501 |
| CH3CH2COCl | " | 2.b.) | " | " | " | " | " | OCOC2H5 | 515 |
| CH3(CH2)2COCl | " | " | " | " | " | " | " | OCO(CH2)2CH3 | 529 |
| CH3(CH2)3COCl | " | " | " | " | " | " | " | OCO(CH2)3CH3 | 543 |
| (CH3)2CHCOCl | " | " | " | " | " | " | " | OCOCH(CH3)2 | 529 |
| (CH3)3CCOCl | " | " | " | " | " | " | " | OCOC(CH3)3 | 543 |
| CH2<br>  \<br>   CH—COCl<br>  /<br>CH2 | " | " | " | " | " | " | " | OCO—CH(CH2/CH2) | 527 |
| H—CH2CH2COCl | " | " | " | " | " | " | " | OCOCH2CH2—H | 583 |
| C2H5OCO—Cl | " | " | " | " | " | " | " | OCO2C2H5 | 531 |
| p-Cl—C6H4—SO2—Cl | " | " | " | " | " | " | " | OSO2—C6H4-p-Cl | 634 |

TABLE 7b

Basic corticoid = Prednisone (Pre-n)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH3CO)2O | Pre-n | 2.a.) | C=O | H | H | H | —CH(CH3)2 | OCOCH3 | 487 |
| CH3CH2COCl | " | 2.b.) | " | " | " | " | " | OCOC2H5 | 501 |
| CH3(CH2)2COCl | " | " | " | " | " | " | " | OCO(CH2)2CH3 | 515 |
| CH3(CH2)3COCl | " | " | " | " | " | " | " | OCO(CH2)3CH3 | 529 |
| (CH3)2CHCOCl | " | " | " | " | " | " | " | OCOCH(CH3)2 | 515 |
| (CH3)3CCOCl | " | " | " | " | " | " | " | OCOC(CH3)3 | 529 |
| CH2<br>  \<br>   CH—COCl<br>  /<br>CH2 | " | " | " | " | " | " | " | OCO—CH(CH2/CH2) | 513 |
| (cyclopentyl-H)—CH2CH2COCl | " | " | " | " | " | " | " | OCOCH2CH2—H | 569 |
| C2H5—OCO—Cl | " | " | " | " | " | " | " | OCO2C2H5 | 517 |
| p-Cl—C6H4—SO2—Cl | " | " | " | " | " | " | " | OSO2—C6H4-p-Cl | 620 |

TABLE 7c

Basic corticoid = Prednisone (Pre-n)

| Reagent: (anhydride or chloride) | Basic corticoid | Process variant Example 2 | A | Y | Z | R(3) | R(2) | R(1) | MS (m/e) M + H+ |
|---|---|---|---|---|---|---|---|---|---|
| (CH3CO)2O | Pre-n | 2.a.) | C=O | H | H | H | —CH2C(CH3)3 | OCOCH3 | 515 |
| CH3CH2COCl | " | 2.b.) | " | " | " | " | " | OCOC2H5 | 529 |

TABLE 7c-continued

| | Basic corticoid = Prednisone (Pre-n) | | | | | | | | |
|---|---|---|---|---|---|---|---|---|---|
| Reagent: (anhydride or chloride) | Basic corticoid | Process variant Example 2 | A | Y | Z | R(3) | R(2) | R(1) | MS (m/e) M + H+ |
| CH₂\<br>   \CH—COCl<br>CH₂/ | " | " | " | " | " | " | " | OCO—CH(CH₂)(CH₂) | 541 |
| C₂H₅OCO—Cl | " | " | " | " | " | " | " | OCO₂C₂H₅ | 545 |
| p-Cl—C₆H₄—SO₂—Cl | " | " | " | " | " | " | " | OSO₂—C₆H₄-p-Cl | 648 |

TABLE 7d

| | Basic corticoid = Prednisone (Pre-n) | | | | | | | | |
|---|---|---|---|---|---|---|---|---|---|
| Reagent: (anhydride or chloride) | Basic corticoid | Process variant Example 2 | A | Y | Z | R(3) | R(2) | R(1) | MS (m/e) M + H+ |
| (CH₃CO)₂O | Pre-n | 2.a.) | C=O | H | H | H | CH₂CH₂OCH₃ | OCOCH₃ | 503 |
| CH₃CH₂COCl | " | 2.b.) | " | " | " | " | " | OCOC₂H₅ | 517 |
| CH₂\<br>   \CH—COCl<br>CH₂/ | " | " | " | " | " | " | " | OCO—CH(CH₂)(CH₂) | 529 |
| p-Cl—C₆H₄—SO₂—Cl | " | " | " | " | " | " | " | OSO₂—C₆H₄-p-Cl | 637 |

Example 6

A solution of 540 mg of prednisolone-17-isobutylcarbonate-21-p-chlorobenzenesulfonate in 5.6 ml of absolute dimethylformamide is treated with 1.04 g of dry lithium chloride and stirred at 100° C. in an N₂ atmosphere for 4 hours. The mixture is poured into 200 ml of aqueous sodium chloride solution, and the precipitate formed is filtered off, dried and crystallized from acetone/methylene chloride/diethyl ether. 420 mg of prednisolone17-isobutylcarbonate-21-chloride are obtained.

Melting point 132° C. MS: m/e=480 [M+H+] TLC: 0.7

In the same manner, prednisolone-17-isopropylcarbonate-21-chloride is obtained from prednisolone-17-isopropylcarbonate-21-p-chlorobenzenesulfonate, prednisolone-17-tert.-butylmethylcarbonate-21-chloride is obtained from prednisolone-17-tert.-butylmethylcarbonate-21-p-chlorobenzenesulfonate and prednisolone-17-methoxyethylcarbonate-21-chloride is obtained from prednisolone-17-methoxyethylcarbonate-21-p-chlorobenzenesulfonate.

Example 7

A solution of 300 mg of prednisolone-17-isobutylcarbonate-21-p-chlorobenzenesulfonate in 3 ml of absolute dimethylformamide is treated with 630 mg of dry lithium bromide and stirred at 110° C. under an N₂ atmosphere for 4 hours. The mixture is poured into 20 ml of aqueous sodium chloride solution, and the precipitate formed is filtered off, dried and chromatographed on silica gel (column dimensions 17×3 cm) using methylene chloride/methanol 99:1 as the eluant. After distilling off the solvent, 310 mg of prednisolone-17-isobutylcarbonate-21-bromide are obtained after crystallization from diethyl ether:

MS: m/e=524 [M+H+]

The same reaction product is obtained if 0.5 g of potassium bromide is employed in the reaction instead of LiBr, the mixture is additionally treated and worked up and the product is prepared in pure form (chromatography).

In the same manner, prednisolone-17-isopropylcarbonate-21-bromide is obtained from prednisolone-17-isopropylcarbonate-21 -p-chlorobenzenesulfonate, prednisolone-17-tert.-butylmethylcarbonate-21-bromide is obtained from prednisolone-17-tert.-butylmethylcarbonate-21-chlorobenzenesulfonate and prednisolone-17-methoxyethylcarbonate-21-bromide is obtained from prednisolone-17-methoxyethylcarbonate-21-p-chlorobenzenesulfonate.

Example 8

A solution of 540 mg of prednisolone-17-isobutylcarbonate-21-p-chlorobenzenesulfonate in 10 ml of absol. dimethylformamide is treated with 1.00 g of dry potassium iodide and stirred at 100° C. in an N₂ atmosphere for 2 hours. The mixture is poured into 200 ml of aqueous sodium chloride solution, a precipitate formed is filtered off, dried and crystallized from acetone/methylene chloride/diethyl ether or chromatographed as indicated in Example 7 for the corresponding 21-bromide. 300 mg of prednisolone-17-isobutylcarbonate-21-iodide are obtained.

Melting point 110° C. MS: m/e=571 [M+H+] TLC: 0.7

In the same manner, prednisolone-17-isopropylcarbonate-21-iodide is obtained from prednisolone-17-isopropylcarbonate-21-p-chlorobenzenesulfonate, prednisolone-17-tert.-butylmethylcarbonate-21-iodide is obtained from prednisolone-17-tert.-butylmethylcarbonate-21p-chlorobenzenesulfonate and prednisolone-17-methoxyethylcarbonate-21-iodide is obtained from prednisolone-17-methoxyethylcarbonate-21-p-chlorobenzenesulfonate.

The same reaction products are obtained if 300 mg of an abovementioned 21-chlorosulfonate are heated to reflux under $N_2$ with 60 mg of lithium iodide in 6 ml of absolute acetone or butan-2-ol for 3 hours, the mixture is poured into 20 ml of $H_2O$ and extracted using methylene chloride and, after customary working-up, the product is crystallized from diisopropyl ether (200–300 mg yield).

Example 9

As in Table 8, the corresponding 21-halide derivatives of the formula I are obtained from the appropriate corticoid-17-alkyl- or 17-methoxyethylcarbonate-21-p-chlorobenzenesulfonates using alkyl halides if the reactions are carried out in the manner as described for Examples 6, 7 and 8:

The characterization of the reaction products can be carried out by thin layer chromatography (TLC); in this case the reaction products have $R_F$ values of about 0.65–0.75. As a rule, the reaction products are characterized by mass spectra using $MS = m/e = \ldots (M+H^+)$ (as a rule FAB spectra).

The $M+H^+$ values were in each case rounded up. IR, $^1H$-NMR and UV spectra can also be used for characterization.

TABLE 8

(see Tables 2–7 for abbreviation for basic corticoids)

| Reagent | Prep. as in Example | Basic corticoid | A | Y | Z | R(3) | R(2) | R(1) |
|---|---|---|---|---|---|---|---|---|
| LiCl | 6 | Dex | CHOH | F | H | $CH_3$ | —CH($CH_3$)$_2$ | Cl |
| LiBr | 7 | " | " | " | " | " | " | Br |
| KI | 8 | " | " | " | " | " | " | I |
| LiCl | 6 | M-pred | CHOH | H | $CH_3$ | H | " | Cl |
| LiBr | 7 | " | " | " | " | " | " | Br |
| KI | 8 | " | " | " | " | " | " | I |
| LiCl | 6 | F-Dex | CHOH | F | F | $CH_3$ | " | Cl |
| LiBr | 7 | " | " | " | " | " | " | Br |
| KI | 8 | " | " | " | " | " | " | I |
| LiCl | 6 | Cort. | CHOH | H | H | H | " | Cl |
| LiBr | 7 | " | " | " | " | " | " | Br |
| KI | 8 | " | " | " | " | " | " | I |
| LiCl | 6 | Pre-n | C=O | H | H | H | " | Cl |
| LiBr | 7 | " | " | " | " | " | " | Br |
| KI | 8 | " | " | " | " | " | " | I |
| LiCl | 6 | Dex | CHOH | F | H | $CH_3$ | —$CH_2$CH($CH_3$)$_2$ | Cl |
| LiBr | 7 | " | " | " | " | " | " | Br |
| KI | 8 | " | " | " | " | " | " | I |
| LiCl | 6 | M-pred | CHOH | H | $CH_3$ | H | " | Cl |
| LiBr | 7 | " | " | " | " | " | " | Br |
| KI | 8 | " | " | " | " | " | " | I |
| LiCl | 6 | F-Dex | CHOH | F | F | $CH_3$ | " | Cl |
| LiBr | 7 | " | " | " | " | " | " | Br |
| KI | 8 | " | " | " | " | " | " | I |
| LiCl | 6 | Cort. | CHOH | H | H | H | " | Cl |
| LiBr | 7 | " | " | " | " | " | " | Br |
| KI | 8 | " | " | " | " | " | " | I |
| LiCl | 6 | Pre-n | C=O | H | H | H | " | Cl |
| LiBr | 7 | " | " | " | " | " | " | Br |
| KI | 8 | " | " | " | " | " | " | I |
| LiCl | 6 | Dex | CHOH | F | H | $CH_3$ | —$CH_2$C($CH_3$)$_3$ | Cl |
| LiBr | 7 | " | " | " | " | " | " | Br |
| KI | 8 | " | " | " | " | " | " | I |
| LiCl | 6 | M-pred | CHOH | H | $CH_3$ | H | " | Cl |
| LiBr | 7 | " | " | " | " | " | " | Br |
| KI | 8 | " | " | " | " | " | " | I |
| LiCl | 6 | F-Dex | CHOH | F | F | $CH_3$ | " | Cl |
| LiBr | 7 | " | " | " | " | " | " | Br |
| KI | 8 | " | " | " | " | " | " | I |
| LiCl | 6 | Cort. | CHOH | H | H | H | " | Cl |
| LiBr | 7 | " | " | " | " | " | " | Br |
| KI | 8 | " | " | " | " | " | " | I |
| LiCl | 6 | Pre-n | C=O | H | H | H | " | Cl |
| LiBr | 7 | " | " | " | " | " | " | Br |
| KI | 8 | " | " | " | " | " | " | I |
| LiCl | 6 | Dex | CHOH | F | H | $CH_3$ | —$CH_2CH_2OCH_3$ | Cl |
| LiBr | 7 | " | " | " | " | " | " | Br |
| KI | 8 | " | " | " | " | " | " | I |
| LiCl | 6 | M-pred | CHOH | H | $CH_3$ | H | " | Cl |
| LiBr | 7 | " | " | " | " | " | " | Br |
| KI | 8 | " | " | " | " | " | " | I |
| LiCl | 6 | F-Dex | CHOH | F | F | $CH_3$ | " | Cl |
| LiBr | 7 | " | " | " | " | " | " | Br |
| KI | 8 | " | " | " | " | " | " | I |
| LiCl | 6 | Cort. | CHOH | H | H | H | " | Cl |
| LiBr | 7 | " | " | " | " | " | " | Br |
| KI | 8 | " | " | " | " | " | " | I |
| LiCl | 6 | Pre-n | C=O | H | H | H | " | Cl |
| LiBr | 7 | " | " | " | " | " | " | Br |
| KI | 8 | " | " | " | " | " | " | I |

Example 10

7 ml of tetraisopropyl orthocarbonate and 0.2 g of p-toluenesulfonic acid are added to a solution of 1.5 g of prednisolone in 45 ml of absolute dioxane. After heating at 60° C. and stirring for 3 to 5 hours, a TLC diagram shows an intense spot having an $R_F$ value of about 0.8 for the expected reaction product and only an extremely poorly visible "spot" for the starting material having an $R_F$ value at about 0.3. The reaction mixture is poured into 500 ml of aqueous sodium chloride solution, and the precipitate is filtered off, washed with water and dried. After recrystallizing from methylene chloride/ethanol/diethyl ether, 1.3 g of prednisolone-17,21-diisopropylorthocarbonate of melting point 185° C. are obtained.

MS=m/e=489 (M+H+) IR=3420, 1730, 1660, 1620, 1600, 1100 cm$^{-1}$ UV: $\lambda_{max}$=242.5 nm, $\epsilon$=15,600

Repetition of the batch which, however, instead of being heated to 60° C. is stirred at 20° C. (room temperature) for 3 hours, gives, after analogous working-up, a reaction product (1.1 g) which is largely identical in all spectral data (for example MS=M+H+=360) with the starting material prednisolone.

TLC: $R_F$=0.3 =very strong spot (=prednisolone), $R_F$ about 0.8 only a veryweak spot visible (=desired reaction product)

Example 11

70 ml of tetraisobutyl orthocarbonate and 2 g of p-toluenesulfonic acid are added to a solution of 25 g of prednisolone in 750 ml of absolute dioxane. After heating at 60° C. and stirring for 5 hours, a TLC diagram shows an intense spot having an $R_F$ value of about 0.8 for the expected reaction product and only an extremely poorly visible "spot" for the starting material having an $R_F$ value at about 0.3. The reaction mixture is poured into 8 l of aqueous sodium chloride solution, and the precipitate is filtered off, washed with water and dried. After recrystallizing from methylene chloride/ethanol/diethyl ether, 38.8 g of prednisolone-17,21-diisobutylorthocarbonate of melting point 113° C. are obtained.

MS=m/e=517 (M+H+) IR=3380, 1750, 1735, 1660, 1615, 1600, 1120, 1090 cm$^{-1}$

Example 12

60 ml of tetra-tert.-butylmethyl orthocarbonate and 2 g of p-toluenesulfonic acid are added to a solution of 25 g of prednisolone in 550 ml of absolute dioxane. After heating at 60° C. and stirring for 6 hours, a TLC diagram shows an intense spot having an $R_F$ value of about 0.8 for the expected reaction product and only an extremely poorly visible "spot" for the starting material having an $R_F$ value at about 0.3. The reaction mixture is poured into 8 l of aqueous sodium chloride solution, and the oily precipitate is filtered off and taken up in methylene chloride, and the organic phase is washed with water, dried and the solvent is distilled off. The oil (35 g) is chromatographed on neutral alumina, activity stage II (column 25×8 cm) using methylene chloride as the eluant (100 ml fractions). The fractions, which shown an $R_F$ value of about 0.8 cm in the TLC, are combined, freed from the eluant by distilling-off and after combining give 14 g of yellowish oily prednisolone-17,21-di-tert.-butylmethyl orthocarbonate.

MS m/e=545 (M+H+)

Example 13

7 ml of tetramethoxyethyl orthocarbonate and 2 g of p-toluenesulfonic acid are added to a solution of 25 g of prednisolone in 500 ml of absolute dioxane. After heating at 60° C. and stirring for 5 hours, a TLC diagram shows an intense spot having an $R_F$ value of about 0.8 for the expected reaction product and only an extremely poorly visible "spot" for the starting material having an $R_F$ value at about 0.3. The reaction mixture is poured into 8 l of aqueous sodium chloride solution and an oily precipitate is filtered off. Additional treatments and preparation in pure form by chromatography as in Example 12. 27.5 g of prednisolone-17,21-dimethoxyethylorthocarbonate of melting point 125° C. (dec.) are obtained (by triturating with diethyl ether)

MS: m/e=521 (M+H+) IR 32 3400, 1725, 1660, 1620, 1600, 1125, 1060 cm$^{-1}$

Example 14

In the same manner as described in Example 10, the following are obtained if the following are employed instead of prednisolone:

from dexamethasone dexamethasone-17,21-diisopropylorthocarbonate,
 MS: m/e=521 (M+H+),
from 6α-methylprednisolone 6α-methylprednisolone-17,21-diisopropylorthocarbonate,
 MS: m/e=503 (M+H+),
from 6α-fluorodexamethasone 6α-fluorodexamethasone-17,21-diisopropylorthocarbonate,
 MS: m/e=539 (M+H+),
from cortisol cortisol-17,21-diisopropylorthocarbonate,
 MS: m/e=491 (M+H+),
from prednisone prednisone-17,21-diisopropylorthocarbonate
 MS: m/e=487 (M+H+),
from cortisone cortisone-17,21-diisopropylorthocarbonate,
 MS: m/e=489 (M+H+),
from Reichstein's substance S [Reichstein's substance S]-17,21-diisopropylorthocarbonate
 MS: m/e=475 (M+H+),
from 6α,16α-dimethylprednisolone 6α,16α-dimethylprednisolone-17,21-diisopropylorthocarbonate
 MS: m/e=517 (M+H+),
from 6α-fluoroprednisolone 6α-fluoroprednisolone-17,21-diisopropylorthocarbonate,
 MS: m/e=507 (M+H+).

Example 15

In the same manner as described in Example 11, the following are obtained if the following are employed instead of prednisolone:

from dexamethasone dexamethasone-17,21-diisobutylorthocarbonate,
 MS: m/e=549 (M+H+),
from 6α-methylprednisolone 6α-methylprednisolone-17,21-diisobutylorthocarbonate,
 MS: m/e=531 (M+H+),
from 6α-fluorodexamethasone 6α-fluorodexamethasone-17,21-diisobutylorthocarbonate,
 MS: m/e=567 (M+H+),
from cortisol cortisol-17,21-diisobutylorthocarbonate,
 MS: m/e=519 (M+H+),
from prednisone prednisone-17,21-diisobutylorthocarbonate
 MS: m/e=515 (M+H+),
from cortisone cortisone-17,21-diisobutylorthocarbonate,
 MS: m/e=517 (M+H+),
from Reichstein's substance S [Reichstein's substance S]-17,21-diisobutylorthocarbonate
 MS: m/e=503 (M+H+), from 6α,16α-dimethylprednisolone 6α,16α-dimethyl-prednisolone-17,21-diisobutylorthocarbonate
MS: m/e=545 (M+H+),
from 6α-fluoroprednisolone 6α-fluoroprednisolone-17,21-diisobutylorthocarbonate,
MS: m/e=535 (M+H+),
from 6α-methyldexamethasone 6α-methyldexamethasone-diisobutylorthocarbonate.

Example 16

In the same manner as described in Example 12, the following are obtained if the following are employed instead of prednisolone:
from dexamethasone dexamethasone-17,21-di-tert.-butylmethylorthocarbonate,
MS: m/e=577 (M+H+),
from 6α-methylprednisolone 6α-methylprednisolone-17,21-di-tert.-butylmethylorthocarbonate,
MS: m/e=559 (M+H+),
from 6α-fluorodexamethasone 6α-fluorodexamethasone-17,21-di-tert.-butylmethylorthocarbonate,
MS: m/e=595 (M+H+),
from cortisol cortisol-17,21-di-tert.-butylmethylorthocarbonate,
MS: m/e=547 (M+H+),
from prednisone prednisone-17,21-di-tert.-butylmethylorthocarbonate
MS: m/e=543 (M+H+).

Example 17

In the same manner as described in Example 13, the following are obtained if the following are employed instead of prednisolone:
from dexamethasone dexamethasone-17,21-dimethoxyethylorthocarbonate,
MS: m/e=553 (M+H+),
from 6α-methylprednisolone 6α-methylprednisolone-17,21-dimethoxyethylorthocarbonate,
MS: m/e=535 (M+H+),
from 6α-fluorodexamethasone 6α-fluorodexamethasone-17,21-dimethoxyethylorthocarbonate,
MS: m/e (M+H+),
from cortisol cortisol-17,21-dimethoxyethylorthocarbonate,
MS: m/e=523 (M+H+),
from prednisone prednisone-17,21-dimethoxyethylorthocarbonate
MS: m/e=519 (M+H+).

We claim:
1. A corticoid-17-alkylcarbonate of the formula I

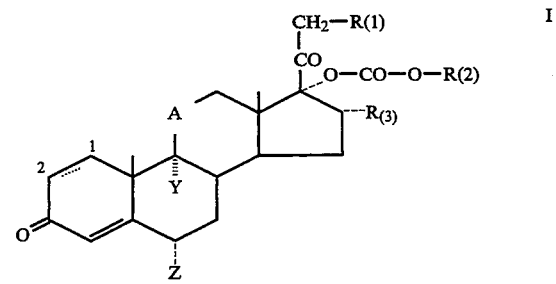

in which:
A is CHOH in any desired steric arrangement, $CH_2$ or $C=O$,
Y is hydrogen, fluorine or chlorine,
Z is hydrogen, fluorine or methyl,
R(1) is O-acyl of the formula II: $-O-CO-(CH_2)_n-R(4)$, oxycarbonyloxyalkyl of the formula III: $-O-CO-O-(CH_2)_n-R(4)$ or alkylsulfonate or arylsulfonate of the formula IV: $-O-SO_2-R(5)$ where R(4) is hydrogen, $(C_1-C_{10})$-alkyl or $(C_3-C_6)$-cycloalkyl R(5) is $(C_1-C_4)$-alkyl, phenyl, chlorophenyl or methylphenyl, n is an integer from 0 to 4,
R(2) is branched $(C_3-C_8)$-alkyl or $-(CH_2)_{2-4}-OCH_3$ and
R(3) is hydrogen or α-methyl.
2. A corticoid-17-alkylcarbonate as claimed in claim 1, wherein
R(1), A, Y, Z, R(3) R(4) and n are as defined in claim 1 and wherein
R(2) is branched $(C_3-C_5)$-alkyl or $(CH_2)_2-OCH_3$ and
R(5) is methyl, ethyl, propyl or phenyl which is unsubstituted or substituted in the p-position by methyl.
3. A pharmaceutical composition for the treatment of dermatoses which comprises an effective amount of a compound I as claimed in claim 1, together with a pharmaceutically acceptable carrier.
4. A method for treating dermatoses, wherein an effective amount of a compound I as claimed in claim 1, combined with pharmaceutically acceptable carriers, is applied to the affected skin site.

* * * * *

UNITED STATES PATENT AND TRADEMARK OFFICE
CERTIFICATE OF CORRECTION

PATENT NO. : 5,362,721
DATED : November 08, 1994
INVENTOR(S) : Ulrich STACHE et al It is certified that error appears in the above-indentified patent and that said Letters Patent is hereby corrected as shown below:

Title Page, item [75]: Line 5 (first line of inventors), the city "Hofheim am Taunus" has been incorrectly printed in boldface.

Claim 1, Column 32, Line 26, after "$(C_3-C_6)$-cycloalkyl", insert --,--.

Claim 2, Column 32, Line 34, after "R(3)", insert --,--.

Signed and Sealed this

Thirtieth Day of May, 1995

Attest:

BRUCE LEHMAN

*Attesting Officer*     *Commissioner of Patents and Trademarks*